US007777876B2

(12) United States Patent
Horai et al.

(10) Patent No.: US 7,777,876 B2
(45) Date of Patent: Aug. 17, 2010

(54) INSPECTION METHOD AND INSPECTION DEVICE

(75) Inventors: Izuo Horai, Odawara (JP); Hirokazu Koyabu, Yokohama (JP); Yuta Urano, Yokohama (JP); Takahiro Jingu, Takasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 224 days.

(21) Appl. No.: 12/167,570

(22) Filed: Jul. 3, 2008

(65) Prior Publication Data

US 2009/0009753 A1    Jan. 8, 2009

(30) Foreign Application Priority Data

Jul. 4, 2007    (JP)    ............................. 2007-176590

(51) Int. Cl.
*G01N 21/00* (2006.01)
(52) U.S. Cl. .................................................. 356/237.3
(58) Field of Classification Search ........................ None
See application file for complete search history.

(56) References Cited

U.S. PATENT DOCUMENTS 5,798,829 A    8/1998    Vaez-Iravani
6,067,154 A *  5/2000    Hossain et al. ............ 356/237.2
6,124,926 A *  9/2000    Ogawa et al. ............. 356/237.4
7,002,677 B2   2/2006    Bevis et al.

* cited by examiner

Primary Examiner—Gregory J Toatley, Jr.
Assistant Examiner—Jarreas C Underwood
(74) Attorney, Agent, or Firm—McDermott Will & Emery LLP

(57) ABSTRACT

An inspection method and an inspection device, or apparatus each capable of conducting composition analysis of a defect detected by elastic or stokes scattered light, an inspection surface or defect on the surface of the inspection surface, or a defect on the surface of the inspection object and its internal composition. A surface inspection method for optically detecting elastic or stokes scattering or inelastic or anti-stokes scattered light from inside the surface of the inspection object, for detecting existence of defects of the inspection object and features of the defects, for detecting positions of the detected defects on the surface of the inspection object, classifying and analyzing the detected defects in accordance with their features on the basis of the positions of the defects and the features of the defects or the classification result of the defects.

19 Claims, 12 Drawing Sheets

TO INELASTIC SCATTERING
DETECTION SYSTEM IN FIG. 1

SIDE VIEW

INSPECTION METHOD AND INSPECTION DEVICE

BACKGROUND OF THE INVENTION

1. Field of the Invention

This invention relates to an inspection method and an inspection device, or apparatus. For example, the invention is suitable for an inspection method and an inspection method for inspecting defects on surfaces and inside of inspection objects such as semiconductor wafers, magnetic disks, liquid crystal substrates, mask substrates, and so forth.

2. Description of the Related Art

To monitor the dust occurring condition of production apparatuses in a production line of a semiconductor substrate (semiconductor wafer), the inspection of defects such as foreign matters adhering to the surface of the substrate, scratches generated during a processing, etc has so far been carried out. In the case of the semiconductor substrate before the formation of a circuit pattern, for example, fine foreign matters and defects having sizes of not greater than dozens of nm on their surface must be carried out. Besides the foreign matters and defects described above, crystal defects existing in a shallow region in the proximity of the substrate surface, surface roughness of the substrate and furthermore, materials that constitute the defect must be analyzed.

An example of the prior art technology for detecting fine defects on the surface of the inspection object such as the semiconductor substrate is described in U.S. Pat. No. 5,798,829. This technology fixedly irradiates a condensed laser luminous flux to the surface of the semiconductor substrate to form an illumination spot having a predetermined size, detects scattered light from a foreign matter occurring when the foreign matter passes through the illumination spot when it adheres to the surface of the semiconductor substrate, and inspects the foreign matters and the defects on the entire surface of the semiconductor substrate.

In this case, scattered light (hereinafter called "background scattered light") always occurs in the illumination spot owing to fine surface roughness (micro-roughness) on the semiconductor wafer even when the foreign matters and the defects do not pass. It is known that shot noise originating from this background scattered light is generally predominant in a noise component of detection signals when fine foreign matters are detected. Since the shot noise is proportional to the square root of light intensity as the base of the noise, the noise level becomes greater substantially in proportion to the square root of the intensity of the background scattered light when the fine foreign matters are detected.

It is well known that when a semiconductor wafer surface is illuminated by P polarization from a low angle of elevation such as a Brewster's angle for a Si crystal in the case of fine foreign matters following the rule of elastic scattering (Rayleigh scattering), on the other hand, scattered light from the foreign matter does not have a strong directivity in an azimuth direction but is scattered in all azimuth directions at a substantially equal intensity.

Background scattered light originating from surface roughness of a semiconductor wafer to which finish polishing is sufficiently made does not exhibit an extremely strong directivity in the azimuth direction, either. In such a case, therefore, it is preferred to uniformly condense and detect the scattered light dispersing in all the azimuth directions in order to secure a high S/N ratio of detection signals. An optical detector of the prior art technology described above collectively receives all of scattered light in the azimuth directions and a preferred S/N ratio can be acquired in this case.

However, the background scattered light originating from the surface roughness (micro roughness) of the semiconductor wafer has in some cases strong directivity. For example, it is known that the background scattered light originating from the surface roughness exhibits strong directivity owing to the correlation between the crystal direction and the illumination direction in epitaxial wafers.

In this case, the output signal of the optical detector that detects the background scattered light originating from the surface roughness in a strong azimuth direction contains greater noise components. Obviously, therefore, it is not advantageous to equally handle the scattered light signal detected at a strong azimuth angle of the background scattered light originating from the surface roughness with the scattered light signal detected at a weak azimuth angle of the background scattered light originating from the surface roughness.

On the other hand, U.S. Pat. Specification No. 7,002,677 describes a technology for partially cutting off scattered light traveling in a specific direction and states that an S/N ratio of a scattered light signal from a foreign matter/defect of an inspection object can be improved by conducting control in such a fashion that an azimuth angle direction in which the background scattered light is partially cut off and an optical detector can receive the scattered light in only an azimuth angle direction in which the background scattered light is weak.

SUMMARY OF THE INVENTION

However, the technology described above does not take into consideration the fact that when excited light is irradiated to a surface of an inspection object, inelastic or anti-stokes scattered light occurs besides the elastic scattered light (Rayleigh scattered light) described above. Recently, the problem has occurred in that when illumination light having a shorter wavelength is irradiated to a surface of a semiconductor wafer to detect ultra-fine defects, the inelastic scattered light (Raman scattering) occurring from the surface reaches a level that can never be neglected with respect to the elastic scattered light (Rayleigh scattered light). Both types of the light occur simultaneously and are received simultaneously without being selected. The S/N ratio of the elastic scattered light occurring from extremely fine defects is lowered by the noise of the inelastic scattered light and it becomes difficult to stably detect the foreign matters and the defects.

Because it is not possible to selectively receive the elastic scattered light and the inelastic scattered light, it is not possible to select only the inelastic scattered light and to conduct property analysis of the inspection object. A detection system alone that applies optical directivity of scattered light has its limit in its discrimination accuracy and detailed analysis is separately required to clarify the original substances of the foreign matter besides the optical detection system.

It is an object of the invention to improve an S/N ratio and to stably detect foreign matters and defects by removing inelastic or anti-stokes scattered light from among scattered light received.

It is another object of the invention to provide an inspection method and an inspection device, or apparatus capable of conducting a composition analysis of a defect and an inspection surface detected by elastic or stokes scattered light or clarifying the defect on the surface of an inspection object and a composition inside the inspection object.

A surface inspection method according to the invention involves the steps of optically detecting either discretely or simultaneously elastic or stokes scattered light and inelastic or anti-stokes scattered light from inside a surface of an inspection object; detecting the existence/absence of a defect and features of the defect of the inspection object; detecting the position of the detected defect on the surface; classifying the detected defect in accordance with the feature; and conducting an analysis of the defect by inelastic or anti-stokes scattered light detection on the basis of the position of the defect and the feature of the defect or the classification result of the defect.

In the inspection method according to the invention, a spectrum of the inelastic or anti-stokes scattered light is subjected to spectroscopic analysis by using the inelastic or anti-stokes scattered light detection and a composition condition of the inspection surface is displayed in a map form by executing a predetermined processing.

An inspection device, or apparatus according to the invention includes optical inspection unit for optically detecting either discretely or simultaneously elastic or stokes scattered light and inelastic or anti-stokes scattered light from a surface of an inspection object or its inside, executes a spectroscopic analysis of a spectrum of the inelastic scattered light by using the inelastic scattered light detection unit of optical unit, executes a predetermined processing and displays a composition condition of the inspection surface in a map form.

In the inspection method according to the invention, a map of a composition condition of the inspection surface by inelastic scattered light detection and a defect map of the inspection surface detected by the elastic scattered light detection are superposed with each other and are visually displayed.

The inspection device, or apparatus according to the invention includes optical inspection unit for optically detecting either discretely or simultaneously elastic scattered light and inelastic scattered light from a surface of an inspection object and its inside; processing unit for detecting the existence/absence of defect of the inspection object and features of the defect from the inspection result by the optical inspection unit, detecting the positions of the detected defects on the surface of the inspection object, classifying the detected defects in accordance with their features, and selecting or designating the defects by conducting defect analysis by inelastic scattered light detection on the basis of the positions of the defects, features of the defects or the classification result of the defects; and inelastic scattered light detection inspection unit of the defect selected or designated by the processing unit.

In the detection of the elastic scattered light (inelastic scattered light), the surface inspection device according to the invention lowers a component of the inelastic scattered light (elastic scattered light) that becomes a noise level by optical unit using a narrow band optical band-pass filter among output signals from an optical detector.

The inspection device according to the invention executes an analysis of a defect by inelastic scattering detection either automatically by a program or in accordance with an instruction of an operator after the optical inspection of the inspection object is made and clarifies the substances of the defect on the basis of the position of the defect by optical inspection and the feature of the defect or the classification result of the defect.

The inspection method according to the invention selects the defect for which the analysis is to be made by using the inelastic scattered light detection in accordance with a predetermined condition determined for the feature of the defect or the classification result of the defect.

The inspection device according to the invention includes defect sampling condition setting unit for conducting inelastic scattering detection in accordance with a predetermined condition for the feature of the defect or the classification result of the defect, defect selection unit for conducting analysis by inelastic scattering detection and unit for setting the priority of the defect for which analysis is to be made by inelastic scattering detection.

The inspection method according to the invention displays the position of the defect and its classification result and designates the defect for which analysis is to be made by inelastic scattering detection among the defects displayed.

The inspection device according to the invention includes display unit for displaying the position of the defect and its classification result and first input unit for designating the defect for which analysis is to be made by inelastic scattering detection among the defects displayed.

The inspection method according to the invention designates a defect for which visual inspection is to be made among the defects displayed, observes the designated defect through an optical microscope or a scanning electron microscope (SEM) and designates the defect for which analysis is to be made by inelastic scattered light detection on the basis of the observation result.

A surface inspection device according to the invention has a function capable of connecting to a review station, and its processing unit has second input unit for designating a defect for which observation through the review station is to be made among the defects displayed on display unit.

The invention can improve the S/N ratio by removing the inelastic scattered light among the scattered light received and can stably detect foreign matters and defects.

Another aspect of the invention provides an inspection method and an inspection device capable of conducting a composition analysis of a defect or inspection surface detected by the elastic scattered light, or capable of clarifying the composition of a defect on an inspection surface or an internal composition of the inspection object by selecting the inelastic scattered light.

DESCRIPTION OF THE EMBODIMENTS

The inspection method and the inspection device, or apparatus according to the invention can be applied to a flat inspection object such as a semiconductor wafer, a glass substrate for a liquid crystal panel, and a mask, a sapphire substrate used for a sensor an LED and a magnetic disk. Explanation of the following embodiments will be given primarily on the case where a semiconductor wafer used in a production process of semiconductor devices is the inspection object.

Embodiment 1

Figure 1:
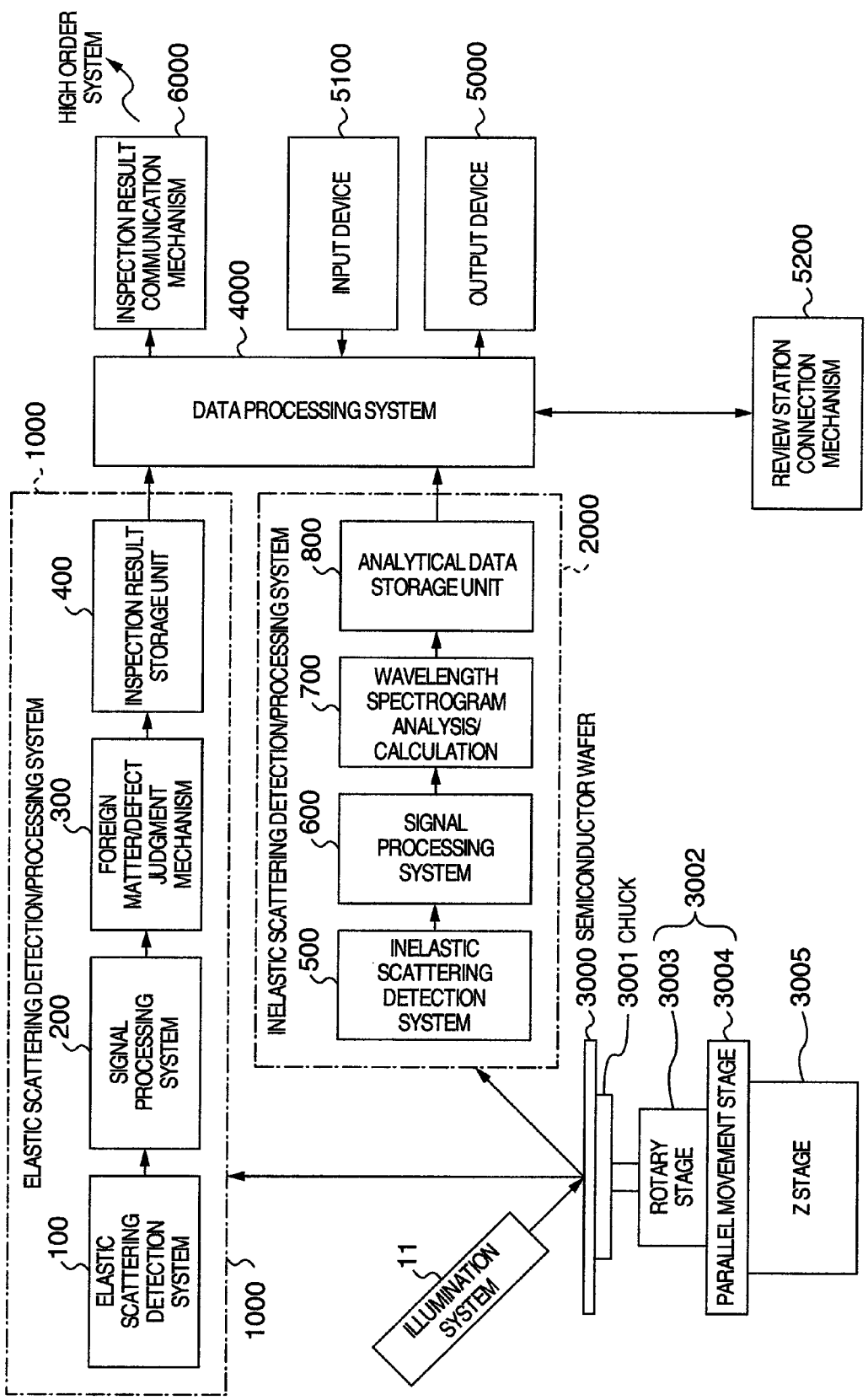
FIG. 1 shows a construction of a surface inspection device, or apparatus according to an embodiment of the invention.

FIG. 1 shows an inspection device using the inspection method according to the first embodiment of the invention.

This embodiment will deal an example where micro-defects are detected by removing inelastic scattered light and detecting and processing elastic scattered light.

The surface inspection device includes an inspection object moving stage 3002, a Z stage 3005, an illumination system 11, an elastic scattering detection processing system 1000 and an inelastic scattering detection processing system 2000, a data processing system 4000 for processing information from each processing system, an output device 5000, an input device 5100, a review station connection mechanism 5200 and an inspection result communication mechanism 6000. The semiconductor wafer 3000 as the inspection object is vacuum adsorbed by a chuck 3001. The chuck 3001 is mounted onto the inspection object moving stage 3002 that includes a rotary stage 3003 and a parallel movement stage 3004, and onto the Z stage 3005. The illumination system 11 for irradiating a laser beam (inspection light) to the surface of the semiconductor wafer 3000 is arranged above the semiconductor wafer 3000.

The inelastic scattering detection processing system 2000 has an inelastic scattering detection system 500, a signal processing system 600, a wavelength spectrum analysis calculation processing system 700 and an analytical data storage unit 800.

The elastic scattering detection processing system 1000 has elastic scattering detection optical system 100, a signal processing system 200, a foreign matter/defect judgment system 300 and an inspection result storage unit 400.

When the laser beam of the illumination system 11 is irradiated to the inspection object, elastic scattered light and inelastic scattered light are emitted from the defect and the surface of the inspected object. In the elastic scattering detection system, the inelastic scattered light is removed, only the scattered light from the defect is detected and fine defects are detected by executing a predetermined processing.

Figure 2:
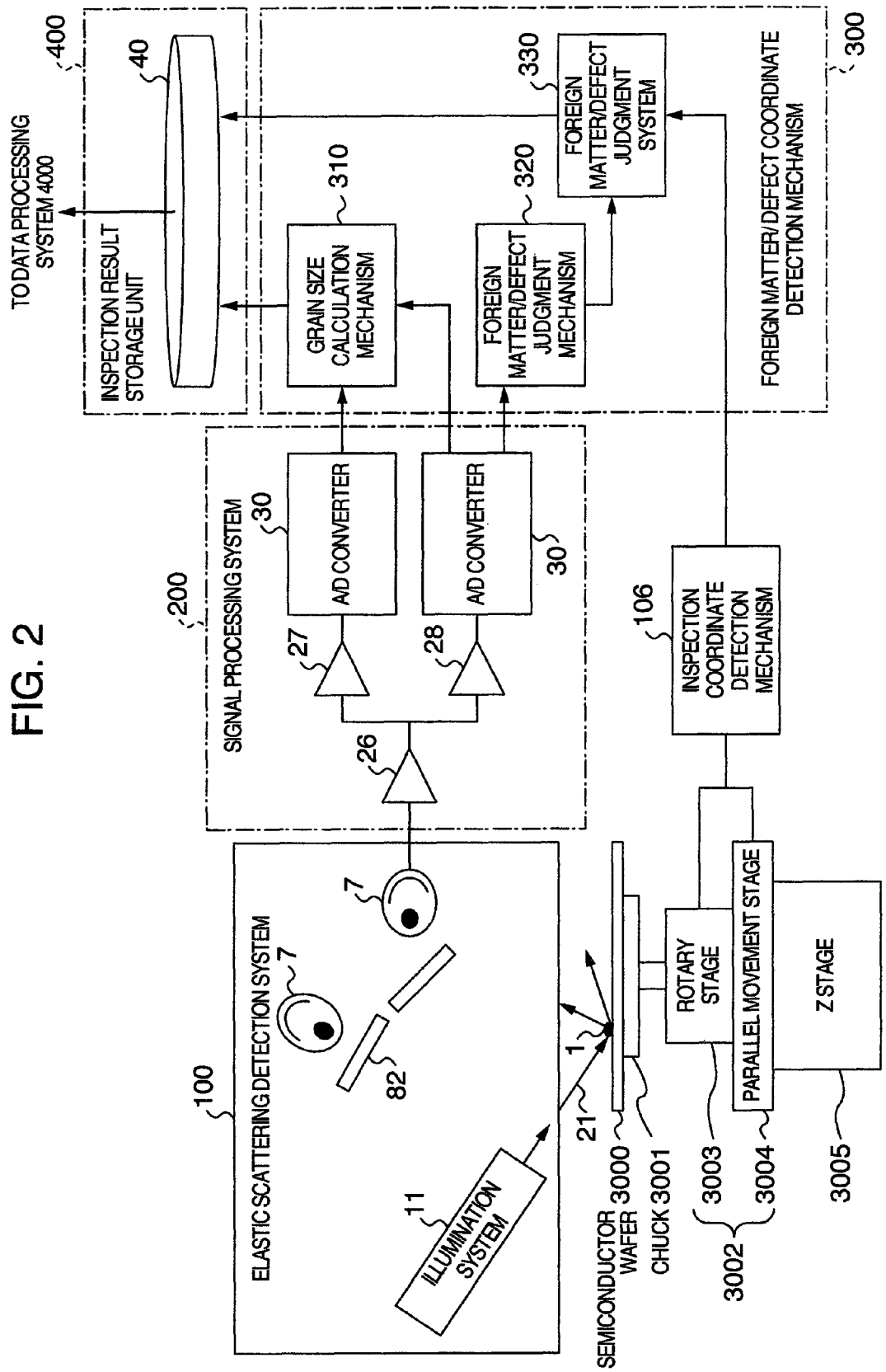
FIG. 2 shows a construction of an elastic scattering detection processing system.

FIG. 2 shows the detail of the elastic scattering detection system 100 in the elastic scattering detection processing system 1000 shown in FIG. 1.

The elastic scattering detection optical system 100 has a light source 11, an optical detector 7, a first elevation angle narrow band optical band-pass filter 72 and a second elevation angle narrow band optical band-pass filter 82. The signal processing system 200 has a pre-amplifier 26, a low band-pass filter 27, a band-pass filter 28 and an A/D converter 30.

The foreign matter/defect judgment system 300 has a grain size calculation mechanism 310, a foreign matter/defect judgment mechanism 320 and a foreign matter/defect coordinates detection mechanism 330. The inspection result storage unit 400 has a data storage unit 40.

A pulse laser that causes pulse oscillation of light of a ultraviolet range repeatedly time-wise is used for the light source 11 of illumination light.

The irradiation beam 21 outgoing from the light source 11 is incident into an illumination lens 18 and forms an illumination spot 3 having a predetermined size. This illumination light is P polarization, for example, and is so arranged as to be incident at a substantial Brewster's angle with respect to crystalline Si into the surface of the semiconductor wafer 3000 as the inspection object.

Therefore, the illumination spot 3 substantially has an elliptic shape. The inside of a profile line in which illumination drops to $1/e^2$ (e: base of natural logarithm) is hereby defined once again as "illumination spot". The width of the illumination spot in the major axis direction is defined as "d1" and the width in the minor axis direction is defined as "d2".

Figure 4:
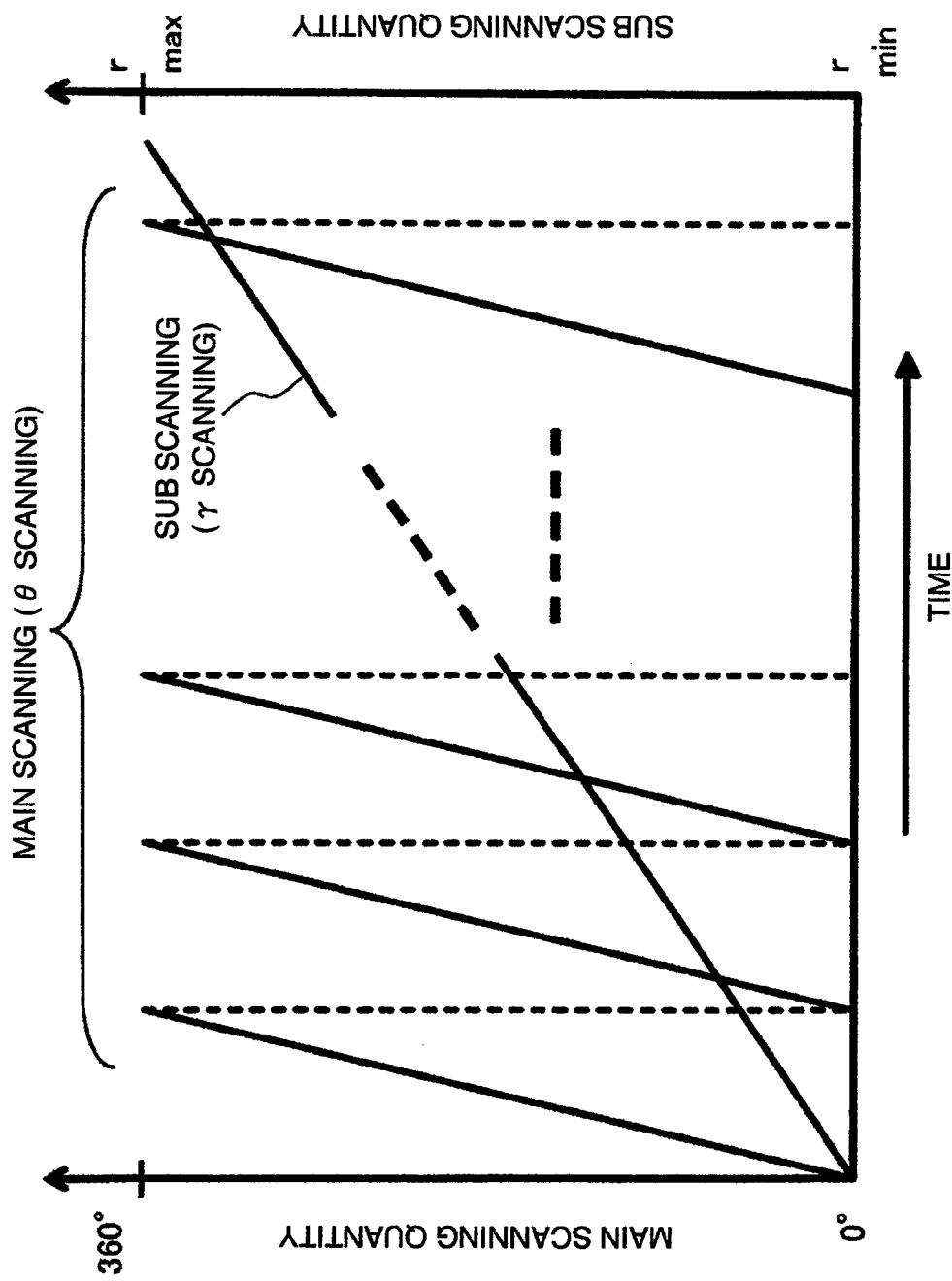
FIG. 4 shows a spiral scanning driving method of an inspection object moving stage

The inspection object moving stage 3002 allows the illumination spot 3 to relatively scan helically on the substantially entire surface of the semiconductor wafer 300 by changing the rotation movement θ as main scanning and parallel movement r as sub-scanning with time in combination as shown in FIG. 4. Sub-scanning moves by Δr while the rotary stage rotates once. When Δr>d1, illumination light is not irradiated in helical scanning on the semiconductor wafer 3000 and gap regions that are not inspected occur. Therefore, sub-scanning is generally set to Δr<d1.

In this embodiment, scanning of the illumination spot 3 is carried out from the inner periphery of the semiconductor wafer 3000 towards the outer periphery or vice versa. In this embodiment, the rotary stage 3003 is driven at a substantially constant angular velocity and the parallel movement stage 3004, at a substantially constant linear velocity, in the substantially full range from the inner periphery to the outer periphery of the semiconductor wafer 3000. To detect the main scanning coordinate position θ and the sub-scanning coordinate position r during the inspection, an inspection coordinate detection mechanism 106 is fitted to the inspection object moving stage 3002.

This embodiment uses an optical read system rotary encoder for detecting the main scanning coordinate position θ and an optical read system linear encoder for detecting the sub-scanning coordinate position r but other detection principles may also be used as long as sensors can precisely detect the angle or the position on the line.

Figure 3A:
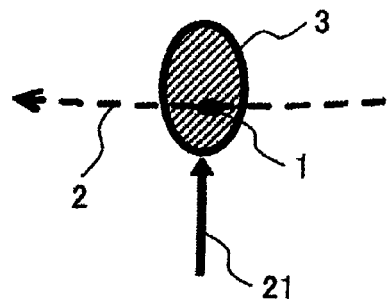
FIGS. 3A, 3B and 3C show a construction of an optical system according to the embodiment.
Figure 3B:
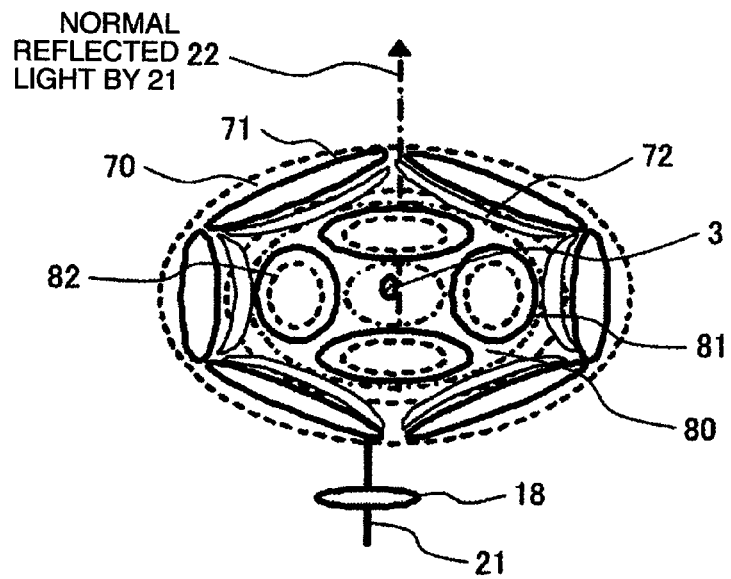
Figure 3C:
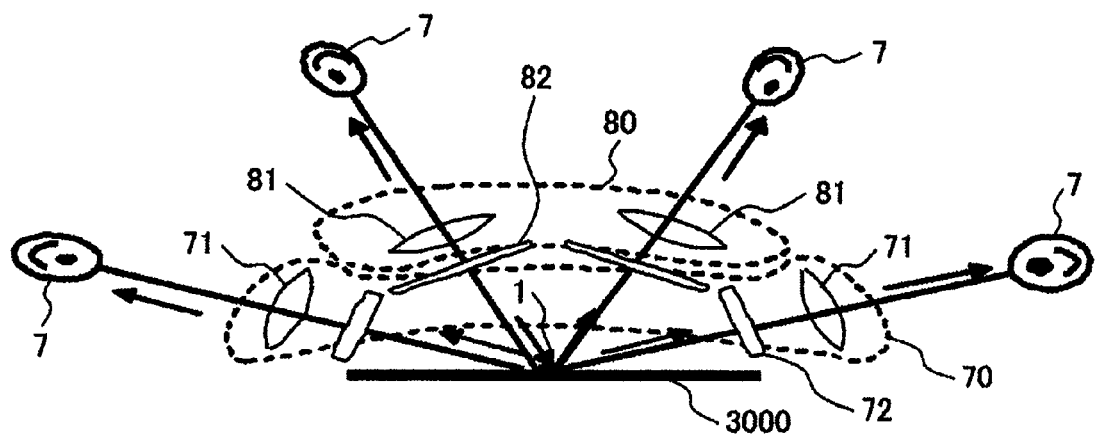

FIGS. 3B and 3C show the detail of the elastic scattered light detection system 100. The elastic scattered light detection system 100 according to this embodiment includes a first elevation angle detection system 70 having six condenser elements 71 that have a first angle of elevation of about 25° so as to efficiently collect scattered light of fine foreign matters causing Rayleigh scattering, are mutually different with respect to the main scanning axis of rotation of the inspection object moving stage 3002 and condense and detect elastic scattered light (scattered, diffracted, reflected light) from six azimuths that are spaced apart from one another by about 60° and a first narrow band optical band-pass filter 72 for removing inelastic scattered light (hereinafter called "Raman scattered light"), and a second elevation angle detection system 80 having four condenser elements 81 that have a second angle of elevation of about 60° and greater than the first angle of elevation, are mutually different with respect to the main scanning axis of rotation of the inspection object moving stage 3002 and condense and detect elastic scattered, diffracted and reflected light) from four azimuths that are spaced apart from one another by about 90° and a second narrow band optical band-pass filter 82 for removing Raman scattered light. Namely, the elastic scattered light detection system 100 has lenses of the ten in total of condenser elements and the narrow band band-pass filters for removing the Raman scattered light that are arranged in front of the lenses.

Incidentally, the narrow band optical band-pass filters may be arranged at the back of the lenses.

This embodiment uses a wavelength of 355 nm for excited light (laser beam). Though the wavelength of the elastic scattered light is the same as the wavelength of excited light (laser beam), the wavelength of the inelastic scattered light occurring simultaneously shifts symmetrically to the right and left with respect to excited light. This is Raman scattered light. The Raman scattered light occurring from the silicon wafer (Si) exhibits a value intrinsic to the material and has a peak at a wavelength of about 520 [cm−1].

Here, the Raman scattered light of 361.6 nm and 348.5 nm occurs with respect to excited light of the wavelength of 355 nm used in this embodiment. These kinds of scattered light are called "stoke scattering" and "anti-stoke scattering", respectively. Since these kinds of scattered light become the noise for the detection of fine defects, the embodiment uses the narrow band optical band-pass filters 72 and 82 of 355 nm±2 nm that mainly permit the passage of 355 nm.

Figure 8:
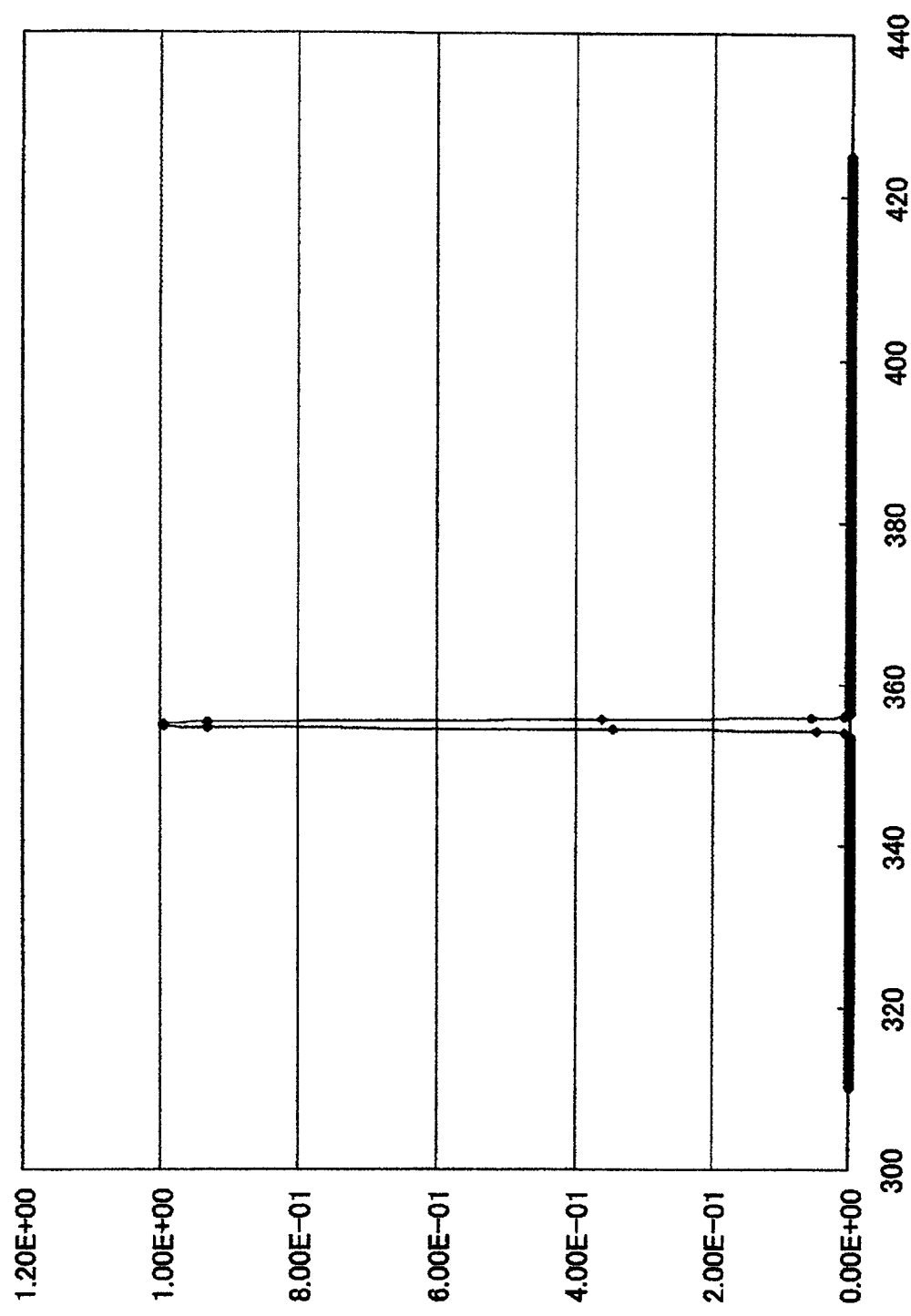
FIG. 8 shows an example of characteristics of a narrow band optical band-pass filter according to the embodiment.

The shift wavelength changes in the inspection objects other than the silicon wafer (Si) because the Raman scattered light exhibits the value intrinsic to the material. Therefore, the band of the narrow band optical band-pass filters 72 and 82 must be naturally changed. FIG. 8 shows an example of the characteristics of the narrow band optical band-pass filter. A preferred filter has a high transmission factor and a low transmission loss.

The mechanical arrangement of each condenser element, particularly, each condenser element of the first elevation angle detection system, may interfere with the irradiation beam 21 and the optical path of its normal reflected light. Therefore, the condenser elements are arranged in such a fashion as to avoid the irradiation beam 21 and the optical path of its normal reflected light in this embodiment.

In this construction, the foreign matter 1 passes through the illumination spot 3 and an output signal corresponding to the intensity of the elastic scattered light (scattered, refracted and reflected light) can be obtained from a plurality of optical detectors 7 through the narrow band optical filters 72 and 82. This embodiment uses a photomultiplier tube for the optical detector 7 but optical detectors based on other detection principles may also be used as long as the detector can detect scattered light from the foreign matter with high sensitivity.

Figure 5:
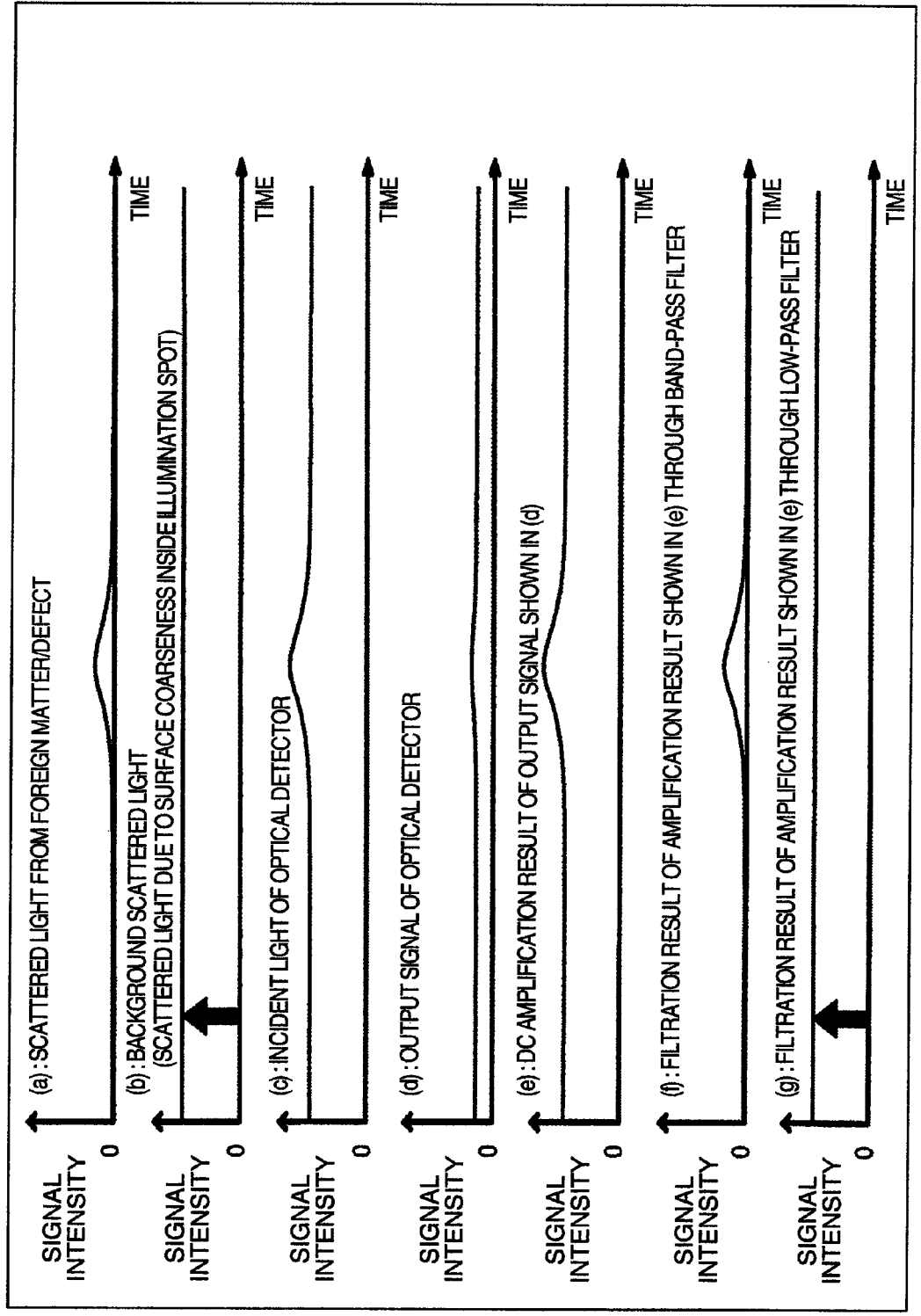
FIG. 5 shows a signal waveform acquired by the surface inspection device according to the embodiment.

As shown in FIG. 2, the output signal from each optical detector 7 is amplified by the pre-amplifier 26 while the output signal substantially keeps a DC signal component contained in the output signal, and is then divided into signals of two systems. The first divided output signal passes through the low band-pass filter 27. The cut-off frequency of this low band-pass frequency 27 is selected so that a pulse-like component that occurs when the foreign matter 1 passes through the illumination spot 3 in the signal (e) shown in FIG. 5 can be removed, and only the DC component is allowed pass through.

As a result, the first signal component obtained as the output of the low band-pass filter 27 becomes the signal that corresponds to the intensity of light mainly originating and occurring from the micro roughness of the surface of the inspection object among the scattered, refracted and reflected light on and in the proximity of the surface of the inspection object.

On the other hand, the second divided output signal passes through the band-pass filter 28. The cut-off frequency of this band-pass filter 28 is selected so that the DC component among the signals (e) shown in FIG. 5 can be removed and only a pulse-like component that occurs when the foreign matter 1 substantially passes through the illumination spot 3 is allowed to pass through.

As a result, the second signal component obtained as the output of the band-pass filter 28 becomes the signal that corresponds to the intensity of light mainly originating and occurring from the foreign matter and the defect on and in the proximity of the surface of the inspection object among the scattered, refracted and reflected light on and in the proximity of the surface of the inspection object.

As described above, the elastic scattering detection system (scattered, refracted and reflected light) according to this embodiment can obtain six sets of combinations of the first and second signal components originating from the output signals of the six optical detectors 7 contained in the first elevation angle detection system 70 and four sets of combinations of the first and second signal components originating from the output signals of the four optical detectors 7 contained in the second elevation angle detection system 80. These first and second signal components are individually sampled by the AD converter 30 and converted to digital data.

Next, the grain size calculation mechanism 310 calculates the sizes of the foreign matters and the defects by using six digital data $b1j$ ($j=1, 2, 3, 4, 5, 6$) in the first elevation angle detection system 70 obtained by converting the second signal component and four digital data $b2j$ ($j=1, 2, 3, 4$) in the second elevation angle detection system 80.

When fine foreign matters are detected, it is known that shot noise originating from the background scattered light is generally predominant in the noise components of the detection signals. The shot noise is proportional to the square root of the intensity of light as the origin. Therefore, the noise level when detecting the fine foreign matter becomes greater in proportion to the square root of the intensity of background scattered light.

In the case where the background scattered light originating and occurring from the surface roughness of the semiconductor wafer 3000 has strong directivity in the azimuth direction, a greater noise component is contained in the output signal of the optical detector detecting that background scattered light at a strong azimuth angle. Therefore, it is obviously not advantageous to equally handle the output signal of the optical detector detecting the background scattered light originating from the surface roughness at a strong azimuth angle with the output signal of the optical detector detecting the background scattered light originating from the surface roughness at a weak azimuth angle.

The grain size calculation mechanism 310 executes a weight addition processing of the digital data bij prepared by converting the second signal component originating from each of the six optical detectors 7 and each of the four optical detectors 7 in accordance with the following formula to acquire a synthetic signal S1 in the first elevation angle detection system 70 and a synthetic signal S2 in the second elevation angle detection system 80.

$$S1 = g11 \times b11 + g12 \times b12 + g13 \times b13 + g14 \times b14 + g15 \times b15 + g16 \times b16 \qquad \text{Exp. 1}$$

$$S2 = g21 \times b21 + g22 \times b22 + g23 \times b23 + g24 \times b24 \qquad \text{Exp. 2}$$

Here, each weight coefficient gij is obtained by multiplying an inverse number of the digital data aij obtained by converting the first signal component originating from each optical detector 7 by a predetermined proportional constant K.

In other words, $$gij = K \times 1/aij \qquad \text{Exp. 3}$$

As described above, the weight coefficient gij, that is, the degree of contribution of the second signal component obtained from each optical detector 7 to the synthetic signals S1 and S2, becomes smaller when the corresponding first signal component is greater. In the case of the optical detector in which strong scattered light occurs owing to directivity of the background scattered light and an S/N ratio gets deteriorated, the degree of contribution to the synthetic signals automatically drops and the S/N ratio of the synthetic signals can be kept at a satisfactory level.

Therefore, when directivity of the background scattered light is strong or when directivity of the background scattered light changes depending on the position on the inspected wafer, the S/N ratio of the synthetic signals can be kept at a satisfactory level even if the relative proportion of the background scattered light in the total scattered light quantity and non-uniformity in the angular direction are not relatively great. Incidentally, the background scattered light described above is the elastic scattered light (Rayleigh scattered light) after the Raman scattered light is removed by the first elevation angle narrow band-pass filter 72 and the second elevation angle narrow band-pass filter 82.

Here, an example with real numbers will be given. Exemplary numerical values assumed in Table 1 are applied to the four optical detectors belonging to the second elevation angle detection system of this embodiment and the result tabulated in the lowermost stage of Table 2 is obtained.

Tables 1 and 2 represent examples of the calculation results of the S/N ratio.

In this case, it can be understood that the S/N ratio obtained by the synthetic signals of this embodiment is better then the system that "detects equally the scattered light in all the azimuth directions" and the system that "cuts off/does not use the azimuth direction in which the background scattered light is strong".

TABLE 1

| | object signal originating from scattered light from foreign matter/defec | background signal originating from background scattered light | noise | S/N ratio |
|---|---|---|---|---|
| detector # 1 | 1.000 | 1.000 | 1.000 | 1.000 |
| detector # 2 | 1.000 | 2.000 | 1.414 | 0.707 |
| detector # 3 | 1.000 | 1.000 | 1.000 | 1.000 |
| detector # 4 | 1.500 | 4.000 | 2.000 | 0.750 |
| #1 to #4 uniform addition | 4.500 | 8.000 | 2.828 | 1.591 |
| only #1 and #3 are added | 2.000 | 2.000 | 1.414 | 1.414 |

TABLE 2

| | object signal originating from scattered light from foreign matter/defec | background signal originating from background scattered light | noise | S/N ratio |
|---|---|---|---|---|
| detector # 1 | 1.000 | 1.000 | 1.000 | 1.000 |
| detector # 2 | 1.000 | 2.000 | 1.414 | 0.707 |
| detector # 3 | 1.000 | 1.000 | 1.000 | 1.000 |
| detector # 4 | 1.500 | 4.000 | 2.000 | 0.750 |
| #1 to #4 uniform addition | 2.875 | 4.000 | 1.658 | 1.734 |

Needless to say, "if the relative proportion of the background scattered light in the total scattered light quantity and non-uniformity in the angular direction are great, the corresponding weight function automatically approaches to zero. Therefore, its effect approaches to the system that "cuts off/does not use the azimuth direction in which the background scattered light is strong". Obviously, a satisfactory S/N ratio can be obtained "when the relative proportion of the background scattered light in the total scattered light quantity and non-uniformity in the angular direction are great", too.

Next, the grain size calculation mechanism 310 converts the synthetic signals S1 and S2 to the sizes of the detected foreign matters and defects. However, because each weight coefficient gij changes whenever the intensity of the first signal component originating from each optical detector changes, the synthetic signals S1 and S2 have mutually different values when the intensity of the background scattered light and its directivity are different at a position on the semiconductor wafer 3000 on which the foreign matter exists.

Therefore, "a calibration curve that associates the sizes of foreign matters/defects and the values of synthetic signals S1 and S2 for the foreign matters is prepared before the start of the inspection and the values of the synthetic signals S1 and S2 that are obtained moment by moment during the inspection are applied to the calibration curve to calculate the sizes of the foreign matters and defects" becomes meaningless.

In the present invention, the synthetic signals S1 and S2 are converted to the sizes of the detected foreign matters and defects in accordance with the following steps.

Step 1:
An operator prepares before the start of the inspection a plurality of calibration wafers to which standard foreign matters (preferably PSL: polystyrene latex spheres) having a known size are allowed to adhere.

Step 2:
The operator sets the inspection condition of the surface inspection device, or apparatus of this embodiment in conformity with the inspection condition of the inspection that is actually carried out for the inspection objects.

Step 3:
The operator starts the inspection of the calibration wafer.

Step 4:
The surface inspection device of this embodiment stores the size of each standard foreign matter detected for each of the ten optical detectors 7 and the relation between the size of each standard foreign matter detected and the value of the digital data that is obtained by converting the second signal component occurring in response to the standard foreign matter.

Step 5:
The surface inspection device of this embodiment generates and stores the calibration curves for the optical detectors 7, that is, ten calibration curves wij (first elevation angle detection system: i=1, 2, 3, 4, 5, 6; second elevation angle detection system: i=2, j=1, 2, 3, 4) from the relation between the size of each of the detected standard foreign matters recorded for each of the ten optical detectors 7 and the value of the digital data prepared by converting the second signal component occurring in response to the standard foreign matter. Here, wij is concretely a function of the following form and the value of wij represents the size of the foreign matter/defect (with the proviso that Iij is intensity of second signal component, pij and qij are calibration curve coefficients).

$$wij(Iij) = pij \times Iij + qij \qquad \text{Exp. 4}$$

The calibration curve preparation work before the inspection is thus completed.

Step 6:

The operator starts the inspection of the actual inspection object wafer.

Step 7:

The surface inspection device of this embodiment generates the synthetic signals S1 and S2 for each of the foreign matters and defects detected by using the expressions 1 to 3.

Step 8:

The surface inspection device of this embodiment generates synthetic calibration curves W1 and W2 from the ten calibration curves wij stored in the optical detectors 7 in accordance with the following expressions.

$$W1 = g11 \times w11 + g12 \times w12 + g13 \times w13 + g14 \times w14 + g15 \times w15 + g16 + w16 \quad \text{Exp. 5}$$

$$W2 = g21 \times w21 + g22 \times w22 + g23 \times w23 + g24 \times w24 \quad \text{Exp. 6}$$

Step 9:

The surface inspection device of this embodiment determines the foreign matter/defect size D1 by applying the synthetic signal S1 to the synthetic calibration curve W1 and the foreign matter/defect size D2 by applying the synthetic signal S2 to the synthetic calibration curve W2.

Step 10:

The surface inspection device of this embodiment employs D1 as the size of the foreign matter/defect detected when the synthetic signal S1 is greater than the synthetic signal S2 and D2 in the opposite case.

Figure 6:
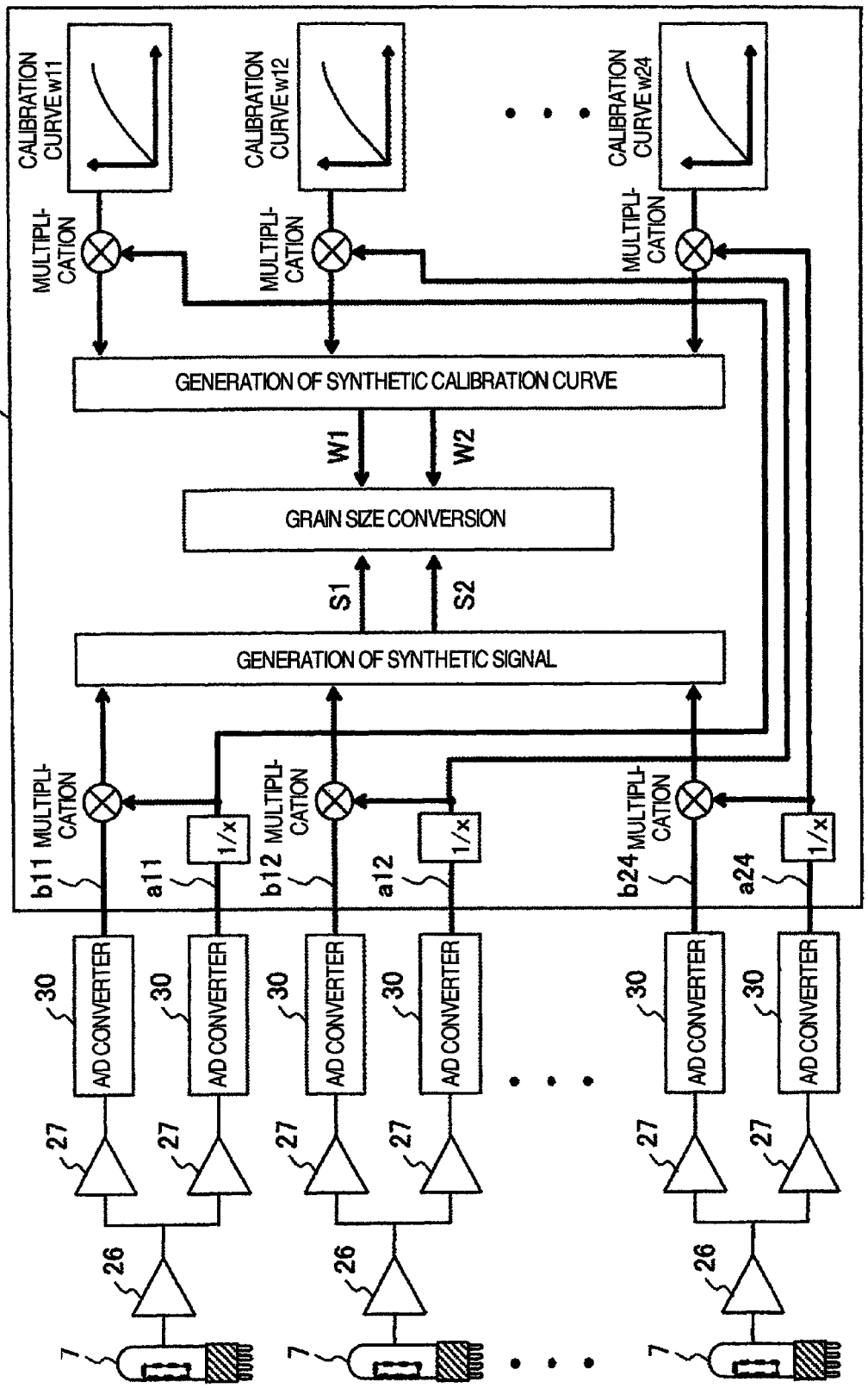
FIG. 6 is a signal processing block diagram of the embodiment.

FIG. 6 is a structural block diagram of the signal processing for generating the synthetic signals S1 and S2 and the synthetic calibration curves W1 and W2.

The grain size calculation mechanism 310 shown in FIG. 6 includes a synthetic signal generation processing unit of signals of the signal processing system 200, a grain size conversion processing unit and a synthetic calibration curve generation unit.

In the surface inspection device of this embodiment, the synthetic calibration curves W1 and W2 synthesizing the calibration curves of each optical detector are generated by using the same weight function as the weight function used for calculating the synthesis signals S1 and S2. Therefore, the relation between the synthetic signals S1 and S2 and the synthetic calibration curves W1 and W2 can be kept always correct. Even when the intensity of the first signal component originating from each optical detector changes and each weight function gij changes, too, conversion of the size of the foreign matter and the defect can be carried out correctly.

In this embodiment, the optical detectors belonging to the detection system having an equal angle of elevation among a plurality of optical detectors are handled as the object of weight addition, but weight addition can be made by including the optical detectors belonging to the detection system of a different angle of elevation. When the size of one foreign matter/defect detected is determined, the inspection result storage unit 410 stores the value of this size, the weight function gij at this time, each digital data aij, bij and the position coordinates of the foreign matter/defect on the semiconductor wafer 300 obtained from the foreign matter/defect coordinate detection system 330.

The defects detected at this time such as scratches, pit defects, foreign matters and their classification result such as size and length are stored in association with coordinate data of the defect positions. When the inspection of the semiconductor wafer 3000 is completed, the result is stored in the inspection result storage unit 400. The information is transferred to the data processing system 4000, the output system 5000 generates the defect map on the basis of the inspection result and the output device 5000 displays the map.

Subsequently, the operator judges whether or not the analysis by the inelastic scattering detection is necessary for an individual defect by watching the defect map displayed on the output device 5000. When the analysis is judged as being necessary, the operator designates the defect by using the input device 5100 (first/second input unit).

Subsequently, the operator judges whether or not observation through an optical microscope or a scanning electron microscope (SEM) of the individual defect through the review station connection mechanism 5200 is necessary. When judging that the observation is necessary, the operator designates the defect requiring the observation through the input device 5100.

When the observation through the optical microscope or the scanning electron microscope (SEM) is necessary, the defect coordinate information designated by the input device 5100 is outputted through the review station connection mechanism. Incidentally, it is assumed hereby that the inspection object is in advance aligned with and set to the review station.

Figure 9:
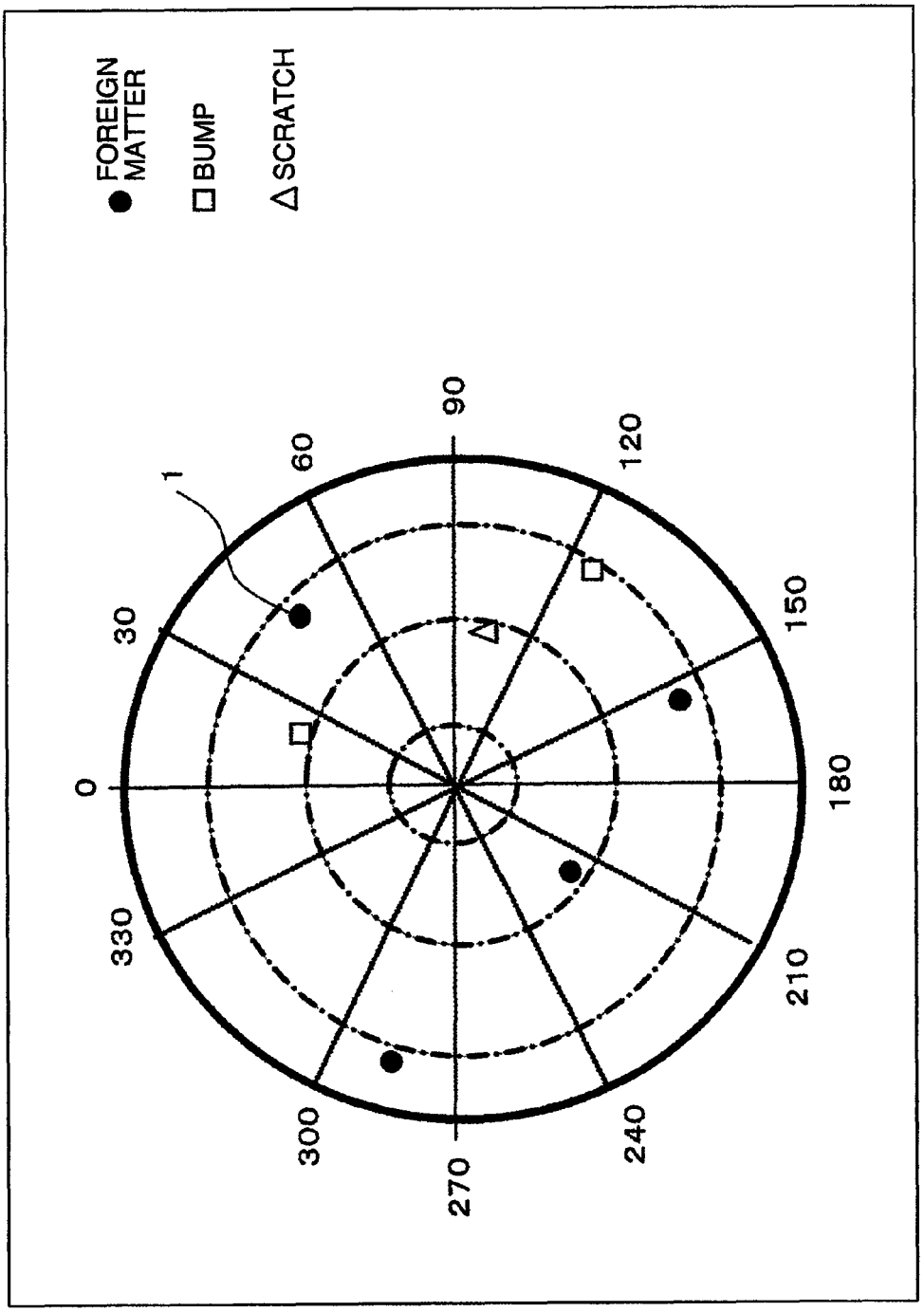
FIG. 9 shows an example of a defect map.

Subsequently, the operator judges whether or not the analysis by the inelastic scattering detection is necessary for an individual defect by watching the defect map or the classification result displayed on the output device 5000 or from the observation result by the review station. When judging that the analysis is as necessary, the operator designates the defect requiring the inelastic scattering detection by using the input device 5100. It will be assumed hereby that a foreign matter represented by a black circle ● on the defect map in FIG. 9 is designated.

When the defect requiring the inelastic scattering detection is designated, the program stored in the data processing system 4000 is executed from the defect information stored in the inspection result storage unit 400 and the inspection object is moved by the inspection object moving stage 3002 below the inelastic scattering detection system 500 shown in FIG. 7. In this embodiment, the inspection object is automatically put onto the inspection object moving stage 3002 by a handling mechanism not shown in the drawing.

Figure 7:
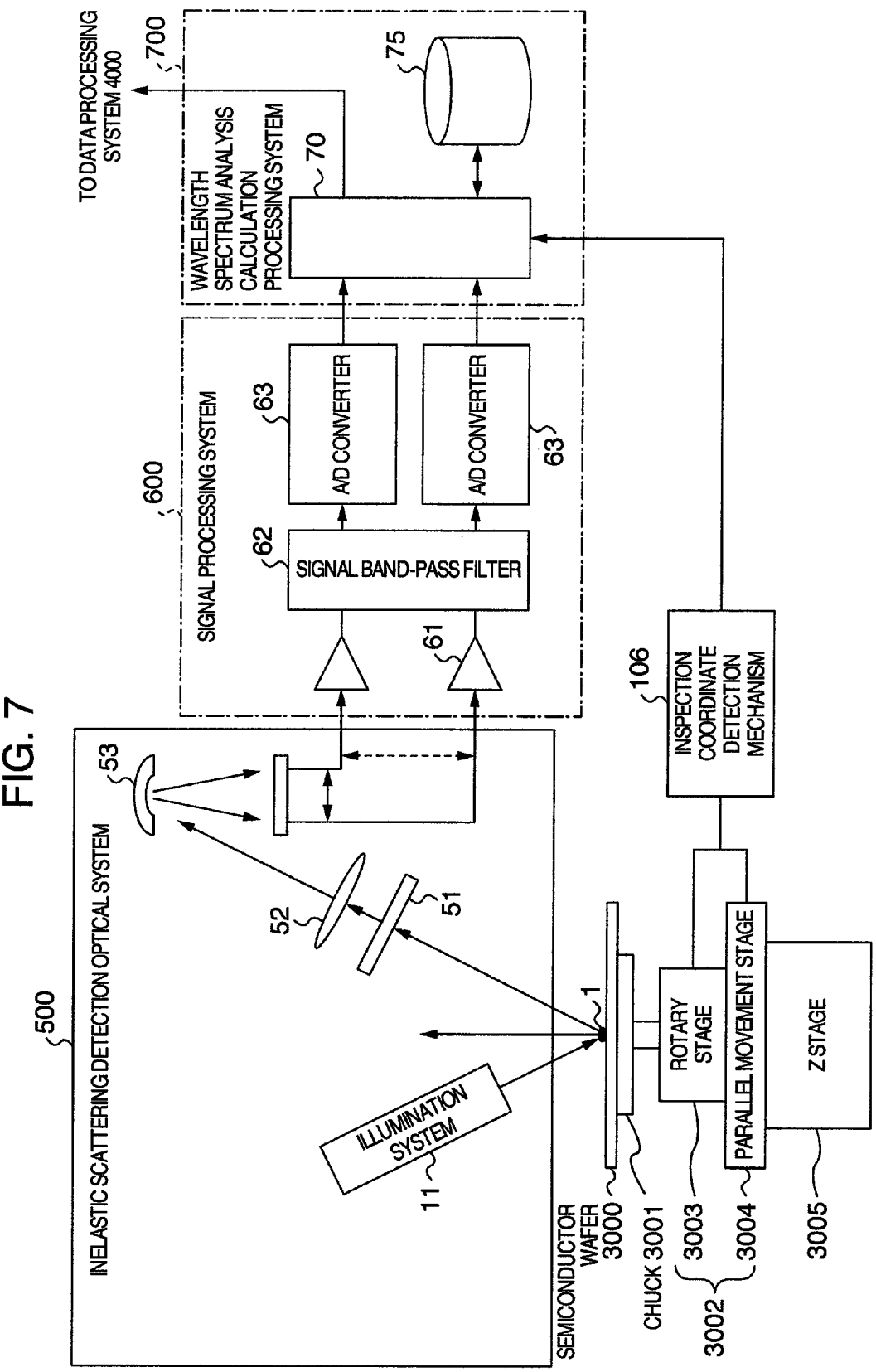
FIG. 7 shows a construction of an inelastic or anti-stokes scattering detection processing system according to the embodiment.

The inelastic scattering detection/processing system 2000 shown in FIG. 7 includes an inelastic scattering detection system 500, a signal processing system 600 and a wavelength spectrum analysis processing system 700.

The inelastic scattering detection system 500 has the foreign matter 1, the narrow band optical band-pass filter 51, the condenser lens 52, a spectroscope element 53 and a multiple detector 54. The signal processing system 600 has a preamplifier 61, a signal band-pass filter 62 and an A/D converter 63. The wavelength spectrum analysis processing system 700 has a first elevation angle detection system 70.

The inspection object moving stage 3002 is moved on the basis of the coordinate data of the position of the defect stored in the inspection result storage unit 400 by the inspection coordinate detection mechanism 106 and the inelastic scattering detection/processing system 200 executes an spectroscopic analysis of, and processes, the Raman spectrum to acquire composition analysis information such as a wave number position, a Raman intensity and a peak width. The result of the analysis is sent to the data processing system 4000 and is displayed on the output device 5000. Incidentally, the detail of the inelastic scattering detection/processing system will be described in Embodiment 2.

Figure 10:
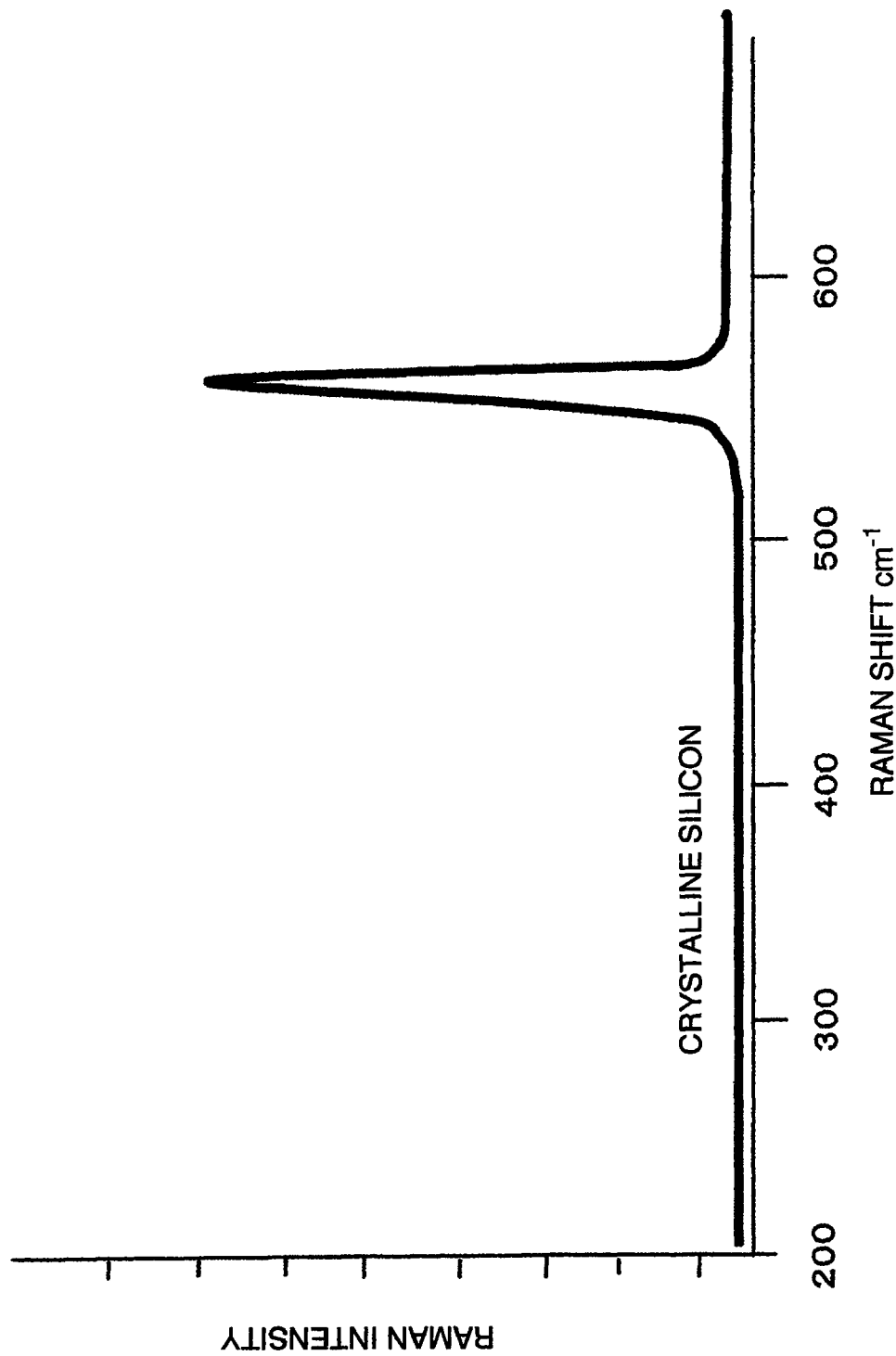
FIG. 10 shows an example of an analytical result by inelastic scattering detection.

FIG. 10 shows an example of the analytical result by the inelastic scattering detection.

The data of the analytical result by the inelastic scattering detection is compared and collated with the data of the material spectral library registered in advance to the analytical data storage unit 75 to judge the material of the designated defect.

The material spectrum registration library has registered thereto the data of spectra of those materials which may be detected by the inelastic scattering detection in consideration of the materials which constitute the inspection object and those materials which may mix during the production process. The data of the analytical result of the defect, the data of the judgment result of the materials of the detect and the classification data of the defect such as the kind of organic and inorganic materials, the kind of metals, the kind of magnetic materials, the kind of semiconductors, the kind of amorphous carbon, and so forth, are stored as the material judgment result of the defect in association with the coordinate data of the position of the defect.

Next, the inspection device has a re-classification function of the defect on the basis of the data of the judgment result of the material of the defect. For example, when the judgment result of the material of the defect is the same as the mother material of the wafer for the defect with sign "1" in the defect map in FIG. 9, the foreign matter is re-classified as a bump (convex type defect) but not as the defect. When the judgment result of the material of the defect is judged as being different from the mother material, on the other hand, the foreign matter is as such re-classified as the defect. Furthermore, the foreign matter can be re-classified more finely in accordance with the kind of the material. The data of re-classification of the defect is stored in association with the coordinate data of the position of the defect.

The inspection result is outputted to the output device 5000 on the basis of the coordinate data of the defect position, the feature data of the defect, the analytical result data of the defect and the data of the material judgment result of the defects that are stored. The inspection result data is transmitted by the inspection result communication mechanism 6000 to a high order system through a communication network. In consequence, the high order system can reproduce the size calculation process for each foreign matter and defect detected and can verify whether or not any abnormality exists in their calculation process. Classification of the defects and abnormality in the production process can be verified more strictly by adding the composition analysis information of each foreign matter and defect.

In the embodiment described above, the operator of the inspection device designates the defect for which the analysis by the inelastic scattering detection is to be made but the defect for which the analysis by the inelastic scattering detection may be automatically selected by the inspection device.

In the embodiment described above, the pulse laser for repeatedly causing time-wise pulse oscillation of light of the wavelength in the ultraviolet region is used as the light source 11 of illumination light. The effects brought forth by this embodiment remain unchanged when laser of a wavelength in the visible region or laser of a continuous oscillation type is used instead. In the embodiment above, each condenser element of the scattered/refracted/reflected light detection system is the lens but a concave mirror may be used, too.

In this case, the insertion position of the narrow band optical band-pass filter for removing the inelastic scattered light (Raman scattered light) is on the front surface of the detector. When the concave mirror is used for the condenser element, each optical axis of the concave mirror can of course avoid the irradiation beam 21 and the optical path of its normal reflected light. Optical interference can be avoided by forming a through-hole through which the optical beam penetrates on each interference mirror surface.

The embodiment described above accomplishes the separation of the first signal component corresponding to the intensity of light mainly originating and occurring from fine concavo-convexities on the surface of the inspection object among rays of light scattered, refracted and reflected on or in the proximity of the surface of the inspection object and the second signal component corresponding to the intensity of light mainly originating and occurring from foreign matters and defects on or in the proximity of the surface of the inspection object by using the low-pass filter and the band-pass filter in the analog circuit before the A/D conversion. Instead, it is also possible to first amplify the output signal from each optical detector while the DC component contained in this signal is held substantially as such, then to execute A/D conversion and to separate the first signal component from the second signal component by executing the low band-pass filtering processing and the band-pass filtering processing in the digital signal processing. In this case, the effects of the embodiment can be obtained similarly.

Still alternatively, the first signal component and the second signal component are separated by using the low band-pass filter and the band-pass filter in the analog circuit before the A/D conversion and then the second signal component is amplified at an amplification ratio that is substantially inversely proportional to the first signal component.

In the optical construction of Embodiment 1 shown in FIG. 3, the example in which the inelastic scattered light is cut off is illustrated for the first elevation angle narrow band optical band-pass filter 72 and the second elevation angle narrow band optical band-pass filter 82. To conduct optimal inspection for a given inspection object, however, the filters may be switched to those which cut off the elastic scattered light for conducting the inspection. The inspection in this case outputs the composition condition inside the inspection object and the composition of the defect on the surface of the inspection object.

Embodiment 2

FIG. 1 shows an inspection device using the inspection method according the second embodiment of the invention. A semiconductor wafer 3000 as an inspection object is vacuum adsorbed to a chuck 3001. The chuck 3001 is mounted onto an inspection object moving stage 3002 and a Z stage 3005 including a rotary stage 3003 and a parallel movement stage 3004.

The surface inspection device includes an illumination system 11, an elastic scattering detection-processing system 1000 and an inelastic scattering detection-processing system 2000, a data processing system 4000 for processing information from each processing system, an output device 5000, an input device 5100, a review station connection mechanism 5200 and an inspection result communication mechanism 6000.

Incidentally, the data processing system 4000, the output device 5000, the input device 5100, the review station connection mechanism 5200 and the inspection result communication mechanism 6000 share the data from the elastic scattering detection/processing system 1000 and the inelastic scattering detection/processing system 2000 and the data from these devices or systems are gathered into one data and are processed by the data processing system 4000.

Embodiment 1 executes the analysis of the defect that is detected by elastic scattering detection and is designated either automatically or through the operator and the inspection result is outputted to the output device 5000 on the basis of the coordinate data of the position of the defect, the data of the feature of the defect and the judgment result data of the material of the defect.

Embodiment 2 represents an example of an analytical device capable of analyzing the properties of the inspection surface by continuously detecting and processing the inelastic scattered light of the inspection surface. In this case, detection of elastic scattering and inspection of inelastic scattering can be selected. When the laser beam 11 is irradiated to the inspection object from the illumination system, the elastic scattered light and the inelastic scattered light are emitted from the defect and the inspection surface. In the inelastic scattering detection system, the spectroscopic device 53 of the inelastic scattering optical system 500 executes wavelength separation, removes the elastic scattered light (Rayleigh scattered light) and allows the passage of only the Raman spectrum originating from the defect and the inspection object.

When photons having a frequency vo are irradiated to a certain molecule, some photons impinge against the molecule while other passes by. Almost all the impinging photons do not change energy and give photons having the same frequency as that of the incident beam. These photons are the elastic scattered light (Rayleigh scattered light). In contrast, only a limited part of the impinging photons cause energy exchange when impinging against the molecule. When the incident photons give energy hv to the molecule, energy of the scattered photons becomes h (vo−v) and the frequency is vo−v.

When the incident photon receives energy hv from the molecule, on the other hand, energy of the scattered photon becomes h(vo+v) and its frequency is vo+v. This is Raman scattering. When the Raman spectrum is subjected to spectroscopic analysis and a predetermined signal processing is executed, information of the wave number position, the Raman intensity and the peak width can be acquired.

FIG. 1 shows the inelastic scattering detection processing system 2000. The detailed construction of the inelastic scattering detection system 500 is the optical system shown in FIG. 7. This illumination system uses the same laser beam 11 as that of the elastic scattering detection processing system 1000. Illumination light is P polarization, for example, and is so constituted as to be incident to the surface of the semiconductor wafer 3000 as the inspection object substantially at a Brewster's angle with respect to crystalline Si.

Therefore, the illumination spot 3 has a substantially elliptic shape and the inside of the profile line in which illumination drops to the square root of e (e: base of natural logarithm) at the center of the illumination spot is defined once again as "illumination spot". The width of this illumination spot in the major axis direction is called "d1" and the width in the minor axis direction, as "d2".

FIG. 7 shows the inelastic scattered light detection processing system. As for normal reflected light 22 irradiated to the inspection object shown in FIGS. 3B and 3C, Rayleigh scattered light is cut off substantially completely by the narrow band optical band-pass filter 51 and only Raman scattered light from the inspection object is allowed to pass and is incident to the spectroscope device 53 through the condenser lens 52 as can be appreciated from the embodiment of the inelastic scattering detection optical system 500.

Incident light is subjected to spectroscopic analysis by the spectroscopic device 53 in accordance with the wavelength shifted and is converted to an electric signal by a multiple detector 54. Here, the spectroscopic device 53 uses grating or diffraction grating. The multiple detector 54 may use a CCD (Charge Coupled Device), an APD array, a TDI sensor or a photo-diode array.

A spectroscope such as a monochromater or a double monochromater using the spectroscopic device 53 in combination with the multiple detector 54 may be used, too. In this case, the narrow band optical band-pass filter 51 is not necessary.

The Raman spectrum converted to the electric signal in FIG. 7 is amplified by the pre-amplifier 61 and is passed through the band-pass filter 62. After the shot noise, etc, is removed, the signal component is sampled by the A/D converter 63 and is converted to the digital data.

In this embodiment, the wavelength spectrum analysis processing 700 includes information having a material spectrum library for determining a composition, registered in advance and an analysis data storage unit 75 for storing the measurement/processing result. The measurement data converted to the digital data is processed and scattering intensity characteristics for the Raman shift and the Raman intensity map for the measurement position are calculated. The result is transferred to the data processing system 4000.

The data processing system displays in the map form the property information of the inspection surface and composition information point-designated by the output device 5000 in such a fashion as to correspond to the Raman intensity in accordance with the contour line and the color. The GUI function for exchanging the information with the operator in the output device 5000 is executed from the input device 5100.

Figure 11:
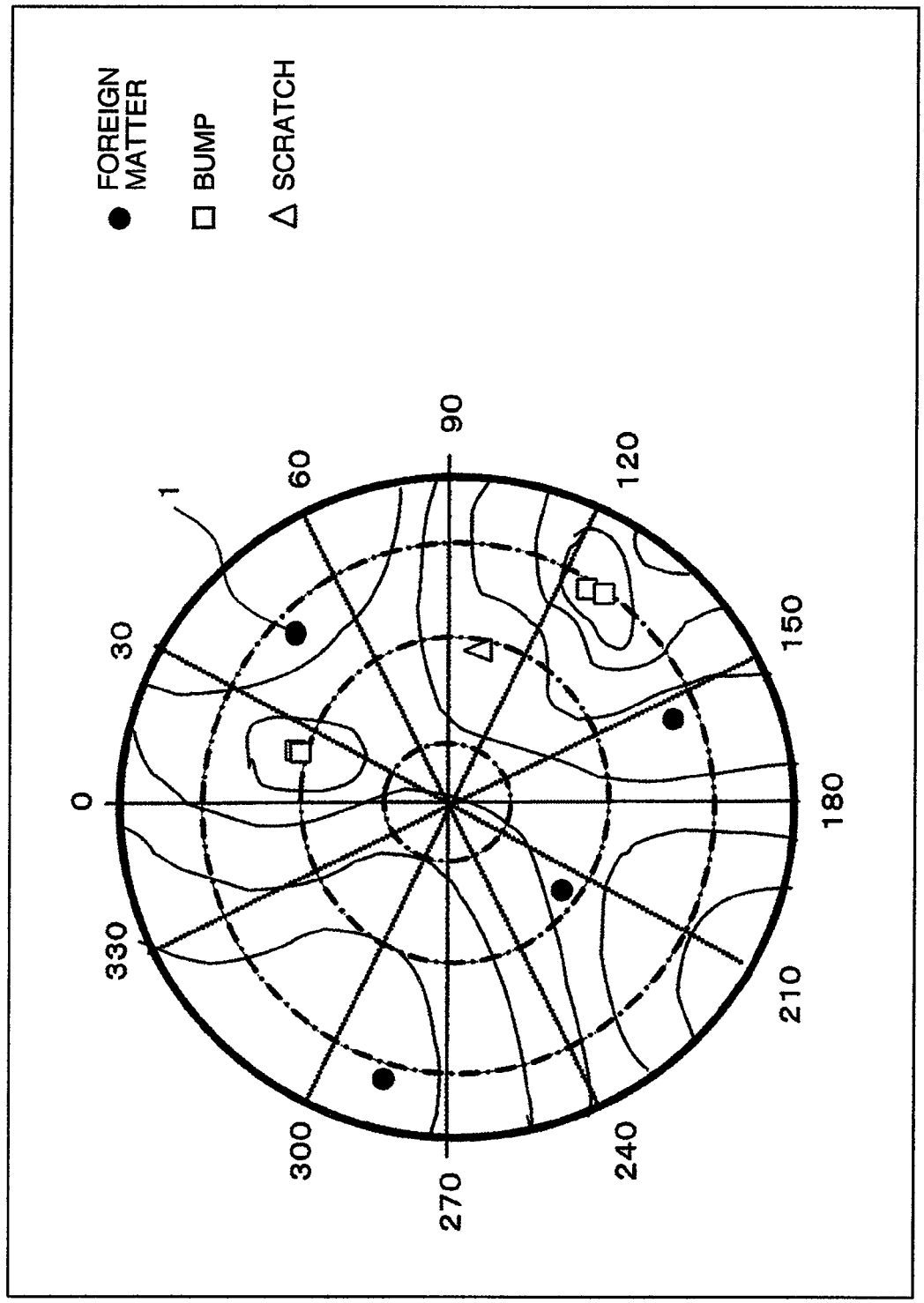
FIG. 11 shows an example of defect maps superposed one upon another.

In the optical construction of the first embodiment shown in FIG. 3, the first elevation angle narrow band optical band-pass filter 72 and the second elevation angle narrow band optical band-pass filter 82 cut off the inelastic scattered light. To conduct optimal inspection depending on the inspection object, however, the inspection may be carried out by switching the band-pass filters to those which cut off the elastic scattered light, on the contrary. Since the inspection does not conduct a spectroscopic analysis in this case, the composition analysis inside the inspection object is not conducted, either, and the composition condition inside the inspection object and on its surface is outputted. FIG. 11 shows a map example by contour lines.

As described above, these kinds of information are transmitted by the inspection result communication mechanism 6000 to the high order system through the communication network.

When inelastic scattering detection is carried out, the semiconductor wafer 3000 as the inspection object is vacuum adsorbed to the chuck 3001. The chuck 3001 is mounted onto the inspection object moving stage 3002 and Z stage 3005 including the rotary stage 3003 and the parallel movement stage 3004.

Rotary movement as main scanning θ and parallel movement r as sub-scanning of the inspection object moving stage 3002 are changed in combination with the passage of time as shown in FIG. 4 so as to scan the illumination spot 3 on the substantial entire surface of the semiconductor wafer 300 relatively and helically. In this case, the speed of the rotary movement θ can be changed arbitrarily. When the Raman scattered light intensity is weak, for example, the rotation speed is lowered to a level at which detection can be made sufficiently and the inspection surface can be inspected continuously without any omission.

Additionally, elastic scattered light detection and inelastic scattered light detection can be executed at the same time. In this case, too, the rotary movement speed and the parallel movement speed can be set to the optimum condition.

The inspection surface is inspected by the data processing system 4000 through inelastic scattering detection and the composition condition of the inspection surface is displayed as the inspection result by the output device 5000 in accordance with the contour line and the color. In consequence, the composition condition can be easily grasped. The entire surface is inspected through elastic scattering detection processing and the inspection result is displayed in the map form by the output device 5000 in accordance with the kind of defects. Both inspection results are gathered by the data processing system 4000 and visual map display can be executed visually by superposing one upon another the respective defect maps.

Furthermore, FIG. 11 displays in the map form the inspection result by elastic scattered light detection in superposition with the inspection result by inelastic scattered light detection.

Black circle ● represents a foreign matter, square □ does a bump and triangle Δ does a scratch. Their existence can be visually grasped on the coordinates in all the azimuth directions.

Figure 12:
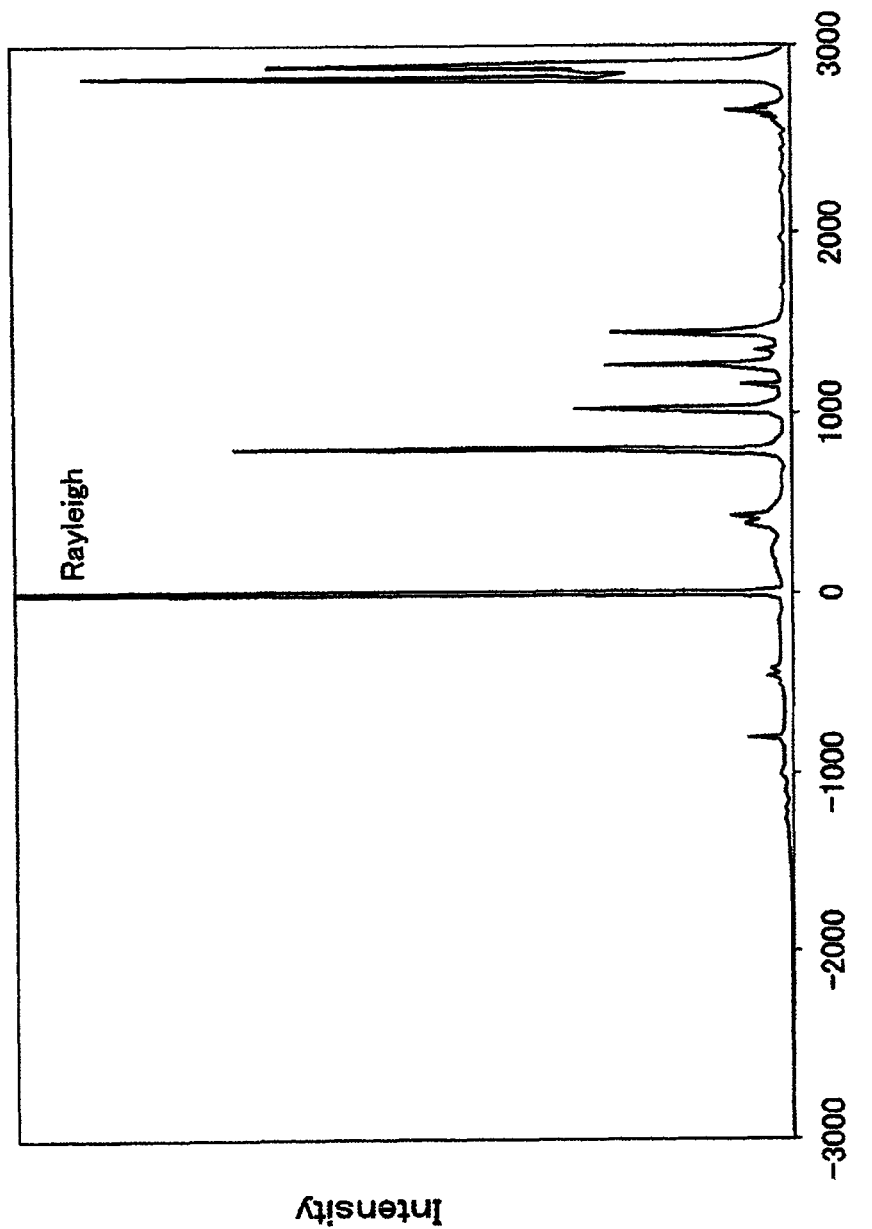
FIG. 12 shows an output intensity of inelastic scattered light (Raman scattered light) and elastic scattered light (Rayleigh scattered light).

FIG. 12 shows the inelastic scattered light (Raman scattered light) and the elastic scattered light (Rayleigh scattering). In other words, the diagram shows the output intensity of the inelastic scattered light (Raman scattered light) and the elastic scattered light (Rayleigh scattering).

FIG. 12 shows the output intensity of forward scattering inclusive of normal reflection received by the light reception device and the point 0 of the abscissa representing the Raman shift is the elastic scattered light (Rayleigh scattering) and the inelastic scattered light (Raman scattered light) can be observed at the points away to the right and left from the point 0. To specify the positions and sizes of foreign matter, bump and scratch, the elastic scattered light (Rayleigh scattering) is observed by cutting off the inelastic scattered light (Raman scattered light).

To specify the materials of the foreign matter and defect, the inelastic scattered light (Raman scattered light) is observed by cutting off the elastic scattered light (Rayleigh scattering).

When these observations are used in combination, the positions and sizes of the foreign matter, the bump and the scratch and their materials can be correctly grasped.

The present invention can be applied to the defect inspection of the surface of various articles such as magnetic disks, liquid crystal substrates, sapphire glass, mask substrates, etc, besides the semiconductor wafers.

The foregoing explanation represents an example of the inspection/analysis device capable of conducting not only the defect inspection on the surface of the semiconductor substrate (wafer) for the production of semiconductors but also the analysis of the properties of the defect, and the inspection/analysis device can be broadly applied to glass substrates used for liquid crystal glass, sapphire substrates used for sensors and LED and glass disk substrates and aluminum disk substrates used for hard disks.

The invention is not particularly limited to the semiconductor production process but can be applied broadly to a variety of production processes such as hard disks, liquid crystal panels and various sensors.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An inspection method comprising the steps of:
   detecting either discretely or simultaneously elastic or stokes scattered light and inelastic or anti-stokes scattered light occurring from a surface and an inside of an inspection object by irradiation of inspection light by deviating them time-wise from each other;
   detecting the existence/absence of a defect of the surface and the feature of said defect by said elastic or stokes scattered light detected;
   detecting the position of said defect on the surface;
   classifying said detected defect in accordance with the feature; and
   conducting an analysis of said defect by said inelastic or anti-stokes scattered light on the basis of the position of said defect, the feature of said defect or the classification result of said defect.

2. An inspection method according to claim 1, wherein noise of said inelastic or anti-stokes scattered light component is lowered in the detection of said elastic or stoke scattered light, and noise of said elastic or stokes scattered light is lowered in the detection of said inelastic or anti-tokes scattered light.

3. An inspection method according to claim 1, wherein noise of said inelastic or anti-stokes scattered light component is lowered among the output signals from an optical detector for detecting said scattered light.

4. An inspection method according to claim 1, wherein noise of said elastic or stokes scattered light component is lowered among the output signals from an optical detector for detecting said scattered light.

5. An inspection method according to claim 1, wherein a defect for which an analysis by said inelastic or anti-stokes scattered light detection is to be made is selected in accordance with a predetermined condition determined for features of said defect or a classification result of said defect.

6. An inspection method according to claim 1, wherein a position of said defect and its classification result are displayed, and a defect for which an analysis by said inelastic or anti-stokes scattered light detection is to be made is designated from among said defects displayed.

7. An inspection method according to claim 6, wherein a defect for which visual inspection is to be made is designated from among said defects displayed, said defect designated is observed through an optical microscope or a scanning electron microscope, and a defect for which an analysis by detection of said inelastic scattered light is designated on the basis of the observation result.

8. An inspection method according to claim 1, wherein re-classification of said defect is carried out in accordance with the result of analysis by said inelastic or anti-stokes scattered light.

9. An inspection method according to claim 5, wherein a map of a composition condition of said inspection surface by inelastic or anti-stokes scattered light detection and a defect map of said inspection surface detected by said elastic or stokes scattered light are superposed with each other and are visually displayed.

10. An inspection apparatus comprising:
    an optical inspection unit for detecting either discretely or simultaneously elastic or stokes scattered light and inelastic or anti-stokes scattered light occurring from the surface of an inspection object and its inside by irradiation of inspection light by deviating them time-wise from each other;
    a processing unit for detecting the existence/absence of defects of said inspection object and features of said defects from the inspection result by said optical inspection unit, detecting the positions of said detected defects on a surface of said inspection object, classifying said detected defects in accordance with their features, and selecting or designating said defects by conducting defect analysis by inelastic or anti-stokes scattered light detection on the basis of the positions of said defects, features of said defects or the classification result of said defects; and an inelastic or anti-stokes scattered light detection inspection unit of said defect selected or designated by said processing unit.

11. An inspection apparatus according to claim 10, wherein said optical inspection unit has a unit for lowering a noise level.

12. An inspection apparatus according to claim 10, wherein said optical detection unit of said elastic or stokes scattered light has a narrow band optical band-pass filter for removing said inelastic scattered light from among output signals from an optical detector.

13. An inspection apparatus according to claim 10, wherein said elastic or stokes scattered light detection unit includes a narrow band optical band-pass filter for removing said elastic scattered light from among the outputs from an optical detector.

14. An inspection apparatus according to claim 10, which has a function capable of selecting a defect for which analysis by said inelastic or anti-stokes scattered light detection is to be made in accordance with a condition determined in advance with the feature of said defect or the classification result of said defect.

15. An inspection apparatus according to claim 10, which further comprises:

a display unit for displaying the position of said defect and the classification result of said defect; and a first input unit for designating a defect for which analysis by said inelastic or anti-stokes scattered light detection is to be made from among said defects displayed by said display unit.

16. An inspection apparatus according to claim 15, which has a connection function with a review station, and wherein said processing unit has a second input unit for designating a defect for which visual inspection is to be made from among said defects displayed on said display unit.

17. An inspection apparatus according to claim 16, wherein said designated defect is observed through an optical microscope or a scanning electron microscope (SEM) and analysis by said inelastic scattered light detection is executed on the basis of the observation result.

18. An inspection apparatus according to claim 10, which has a function capable of classifying again said defects in accordance with the analytical result of said defects by said inelastic scattered light detection.

19. An inspection apparatus according to claim 13, wherein a map of a composition condition of said inspection surface by inelastic or anti-stokes scattered light detection and a defect map of said inspection surface detected by said elastic or stokes scattered light are superposed with each other and are visually displayed.

* * * * *